United States Patent [19]
Brandeis et al.

[11] 3,983,043
[45] Sept. 28, 1976

[54] MIXTURES OF METHYLOLALKYL UREAS AND THEIR BUTYL ETHERS

[75] Inventors: Johann Brandeis, Limburgerhof; Joachim Kurze, Leutershausen, both of Germany

[73] Assignee: BASF Aktiengesellschaft, Ludwigshafen (Rhine), Germany

[22] Filed: Apr. 17, 1974

[21] Appl. No.: 461,502

[30] Foreign Application Priority Data
Apr. 21, 1973 Germany............................ 2320302

[52] U.S. Cl. ................................. 252/8.8; 252/8.9; 260/404; 260/553 R; 8/181; 8/185
[51] Int. Cl.² ..................................... D06M 13/18
[58] Field of Search ............. 260/70 A, 404, 553 R; 252/8.8, 8.9; 427/390; 8/181

[56] References Cited
UNITED STATES PATENTS

| | | |
|---|---|---|
| 1,902,889 | 3/1933 | Paquin ................................... 8/131 |
| 2,361,185 | 10/1944 | Engelmann et al. ................. 260/404 |
| 3,310,416 | 3/1967 | Schibler ......................... 260/70 A X |
| 3,392,150 | 7/1968 | Groll ............................. 260/70 A X |
| 3,489,718 | 1/1970 | Goullon et al. ................. 260/70 A X |
| 3,709,657 | 1/1973 | Hollies et al. ...................... 427/390 |

OTHER PUBLICATIONS

Marsh, *Crease Resisting Fabrics*, p. 59, (Reinhold, 1962).
Ellis, *The Chem. of Synthetic Resins*, pp. 663–664, (Reinhold, 1935).

*Primary Examiner*—Carman J. Seccuro
*Attorney, Agent, or Firm*—Johnston, Keil, Thompson & Shurtleff

[57] ABSTRACT

Mixtures of methylolalkyl ureas containing higher alkyl radicals and their butyl ethers, a process for their manufacture, and their use as softening agents for cellulose fibers. This application discloses and claims subject matter described in German Patent Application P 23 20 302.3, filed Apr. 21, 1973, which is incorporated herein by reference.

3 Claims, No Drawings

MIXTURES OF METHYLOLALKYL UREAS AND THEIR BUTYL ETHERS

U.S. Pat. No. 2,361,185 discloses, inter alia, the reaction of monomethylol compounds of longer-chain alkyl ureas (mention is made of octadecylureidomethanol) or a mixture of the corresponding alkyl ureas themselves and formaldehyde with aliphatic alcohols, such as methanol, ethanol, isopropanol and octanol, in the presence of acid catalysts. The resulting ethers are recommended for use as, for example, textile softeners. It has been found, however, that these products give an unsatisfactory greasy handle on cellulose fibers.

It is an object of the invention to provide softeners capable of imparting a pleasant handle to textiles.

We have now found that the aforementioned drawback does not occur when using the products of the invention. These products are mixtures consisting of a. at least one mono- and/or di-methylolalkyl urea having from 12 to 22 carbon atoms in the alkyl radical and b. at least one butyl ether of a mono- and/or di-methylolalkyl urea having from 12 to 22 carbon atoms in the alkyl radical, the ratio of (a) to (b) in said mixtures being from 2:1 to 1:2, by weight.

Such mixtures may be obtained, for example, by preparing the components (a) and (b) separately in conventional manner, for example as described in said U.S. patent, the disclosures thereof being incorporated herein by reference, and then mixing said components in the above proportions. However, it is far more advantageous to prepare the mixtures by the method of the present invention by reacting at least one alkyl urea having from 12 to 22 carbon atoms in the alkyl radical with from one to three times the molar amount of formaldehyde and from one to six times the molar amount of at least one butanol in a neutral to slightly alkaline medium at elevated temperature until no further water is liberated, distilling off the water of reaction and any water which may have been introduced with the starting materials and then distilling off the excess butanol.

The ($C_{12-22}$ alkyl) ureas necessary as starting materials for the process of the invention are known compounds or are compounds which, though they may not have been expressly described, are obtainable by known processes, for example by transamidation of unsubstituted urea with ($C_{12-22}$ alkyl)amines or by reaction of such amines with cyanuric acid or salts thereof and partial hydrolysis of the resulting alkyl cyanamide. Examples of alkyl ureas of the above kind are dodecyl, tridecyl, hexadecyl and octadecyl ureas. Of particular significance industrially are mixtures of alkyl ureas such as are obtained by processing fatty amines obtained from natural sources such as coconut oil amine, palm kernel oil amine and tallow oil amine. Such alkyl urea mixtures generally contain minor amounts of alkyl ureas in which the alkyl groups have less than 12 or more than 22 carbon atoms. However, the presence of these small amounts does not impair the usefulness of the mixtures as starting materials.

In the process of the invention, the formaldehyde may be used as such or, preferably, it is used in the form of a commercially available aqueous solution or in the form of its dissociable polymers such as paraformaldehyde and trioxylmethylene. Suitable butanols are any of the non-tertiary isomers, preferably either of the two primary isomers butanol-1 and methylpropanol-1 or, if desired, a mixture of different butanols.

Adjustment of the reaction mixture to a neutral to slightly alkaline pH, i.e. a pH of from 7 to about 9, may be effected with any desired alkaline-reacting substance, normally used for this purpose, preferably with low molecular weight amines of low volatility such as, in particular, trialkanolamines of up to 10 carbon atoms.

The reaction mixture is heated to reflux and the water formed and also the water originally present in the reaction mixture is removed by separation from the reflux stream. The butanol may serve as entraining agent for the water if the incomplete separation of water due to the solubility thereof in butanol can be accepted. Better results are obtained if an additional entraining agent of low water miscibility is added to the reaction mixture. For example, toluene and xylene have proved suitable for this purpose when used in amounts of from about 5 to 15% of the butanol.

The reaction is complete when no further water can be separated. The excess butanol and any additional entraining agent used are then distilled off. It is recommended that this operation be carried out under reduced pressure in order to achieve removal as completely as possible. For example, we have successfully used a pressure of from 25 to 40 millibars and a temperature of up to about 130°C.

The resulting mixtures may be used as washproof softeners for cellulose fibers without further purification, either as such or together with other textile finishing agents. We prefer to use them together with cross-linkers such as formaldehyde/urea derivatives, formaldehyde/propylene derivatives, formaldehyde/ethylene urea derivatives, formaldehyde/melamine derivatives and formaldehyde/glyoxal mono-imidazolid-2-one derivatives with or without catalysts such as ammonium and metal salts of inorganic acids.

Particularly suitable substrates are textiles of rayon staple, rayon, cotton and linen and blends of these fibers with each other and with synthetic fibers.

The mixtures of the invention may be used from organic solvents or, preferably, in the form of their aqueous dispersions. Preparation of the emulsion is effected in conventional manner, for example as follows: 200 parts of a mixture of the invention are melted at 50°C and dispersed in a solution of 12 parts of the sodium salt of the sulfuric acid half-ester of an adduct of 25 moles of ethylene oxide and 1 mole of sperm oil alcohol in 788 parts of water using a high-speed stirrer at a solution temperature of 50°C. The emulsion is then homogenized at the same temperature and cooled, this being repeated twice, using a homogenizing machine at superatmospheric pressure of 150 bars. Some of the water may be replaced by organic solvents such as alcohols, ketones, chlorohydrocarbons or gasoline.

Application is preferably effected from a short liquor (by padding) at rates of from 2 to 12 g/l of the mixture of the invention (in terms of active ingredient) to give a wet pickup of from 50 to 120% by weight, this being equivalent to a rate of application of the mixture of the invention to the textile material of from 0.1 to 1.4% by weight (in terms of active ingredient). Alternatively, application may be made from a long liquor, in which from 0.3 to 2 g/l of softener (in terms of active ingredient) are used.

EXAMPLE 1

970 Parts by weight of aqueous formaldehyde solution containing 375 parts by weight of formaldehyde (12.5 moles) are mixed with 10 parts by weight of triethanolamine. To this there are added 740 parts by weight of butanol (10 moles), 80 parts by weight of toluene and 1,450 parts by weight of commercial stearyl urea (4.8 moles, molecular weight 302; $C_{18}:C_{16}$ = 70:30), by weight. The mixture is stirred under mild reflux for 1 hour at about 92°–93°C, the water acting as solvent and the water of reaction being distilled off from the reflux stream. A butanol/toluene mixture is continuously refluxed. Water-separation is virtually complete when 797 parts of water have been separated. The excess butanol is then distilled off under progressively reduced pressure until a full filter-pump vacuum of about 25 millibars has been reached, the bottoms temperature being raised to 130°C.

Yield: 1,855 parts by weight. At room temperature, the product has the consistency of peanut butter.

Formaldehyde content: 12.6% (calculated as formaldehyde in analysis).

Butoxy content: 15.1%.

From the above it is seen that 49.2% of the oxymethylene groups have reacted with the butanol.

EXAMPLE 2

Rayon staple fabric is levelled at a liquor ratio of 1:30 with 2 g/l of a 20% aqueous dispersion of the product described in Example 1, for 15 minutes at 45°C, spun to a residual moisture content of 100%, dried at 80°C in an air drying cabinet, heated for 5 minutes at 125°C and finally conditioned.

Compared with untreated material, the fabric has a soft and very smooth handle, which remains after laundering 5 times at 40°C according to DIN 53,920 (draft).

EXAMPLE 3

Cotton fabric is padded with a liquor consisting of 125 g/l of a 50% aqueous solution of N,N'-dimethylol-hexahydropyrimidinone, 20 g/l of $MgCl_3.6H_2O$ and a. no softener, or
b. 20 g/l of a 20% aqueous dispersion of the product described in Example 1.

The pH of the liquor is from 5 to 5.5 and the wet pickup is 75% by weight. The fabric is then dried at 110°C and condensed for 4 minutes at 150°C and then conditioned.

Assessment of handle a. coarse and relatively hard;
b. soft and very smooth.

Assessment of handle after 5 boils at 93°C according to DIN 53,920 (draft):

a. coarse, rough and moderately soft;
b. soft, smooth; virtually no difference from unwashed material finished with said softener.

EXAMPLE 4

Fabric consisting of a 50:50 cotton/polyester blend is padded with a mixture of water and 80 g/l of a 45% aqueous solution of 1,3-dihydroxy-4,5-dimethylolimidazolidone,
10 g/l of $ZnCl_2$ and
a. no softener, or
24 g/l of a 20% aqueous methanolic dispersion of the product described in Example 1.

The pH of the liquor is from 5 to 5.5 (adjusted with acetic acid) and the wet pickup is 65% by weight. The fabric is then dried at 110°C, condensed for 4 minutes at 150°C and then conditioned.

Assessment of handle a. coarse and rough;
b. very soft and smooth.

Assessment of handle after 5 hot washes (coloreds) at 60°C according to DIN 53,920 (draft):

a. coarse and rough;
b. soft and smooth; virtually no difference from unwashed material treated with said softener.

EXAMPLE 5

Fabric of a 50:50 blend of regenerated cellulose fibers and polyester fibers is padded with an aqueous liquor containing 50 g/l of dimethylol urea, 3 g/l of $NH_4Cl$ and a. no softener, or
b. 20 g/l of a 20% aqueous/methanolic dispersion of the product described in Example 1.

The pH of the liquor is 6 and the wet pickup is 65% by weight. The treated fabric is then dried at 110°C, condensed for 4 minutes at 150°C and then conditioned.

Assessment of handle a. coarse and rough;
b. very soft and smooth.

Assessment of handle after 10 washes (fines) at 40°C according to DIN 53,920 (draft):

a. coarse but slightly less rough;
b. virtually no change.

We claim:

1. A composition of matter consisting essentially of a mixture of
   a. at least one mono- and/or di-methylolalkyl urea having from 12 to 22 carbon atoms in the alkyl radical and
   b. at least one butyl ether of a mono- and/or di-methylolalkyl urea having from 12 to 22 carbon atoms in the alkyl radical, the ratio of (a) to (b) in said mixture being from 2:1 to 1:2 by weight.

2. A process for the manufacture of a mixture of matter as claimed in claim 1, wherein at least one alkyl urea having from 12 to 22 carbon atoms in the alkyl radical is reacted with from 1 to 3 times the molar amount of formaldehyde and from 1 to 6 times the molar amount of at least one butanol in a neutral or slightly alkaline medium at elevated temperature until no further water is liberated, distilling off the water of reaction and any water which may have been introduced with the starting materials and distilling off the excess butanol.

3. A process as claimed in claim 2, wherein an additional entraining agent for distillation of the water is added to the reaction mixture and is distilled off together with the excess butanol.

* * * * *